(12) United States Patent
Yamaguchi et al.

(10) Patent No.: US 9,249,417 B2
(45) Date of Patent: Feb. 2, 2016

(54) REAGENT KIT HAVING ACIDIFIED POLVETHVLENDIMINE FOR INTRODUCTING NUCLEIC ACIDS INTO CELLS

(71) Applicant: National University Corporation Chiba University, Chiba (JP)

(72) Inventors: Naoto Yamaguchi, Chiba (JP); Yasunori Fukumoto, Chiba (JP)

(73) Assignee: National University Corporation Chiba University, Chiba (JP)

( * ) Notice: Subject to any disclaimer, the term of this patent is extended or adjusted under 35 U.S.C. 154(b) by 0 days.

(21) Appl. No.: 13/936,259

(22) Filed: Jul. 8, 2013

(65) Prior Publication Data

US 2013/0292606 A1 Nov. 7, 2013

Related U.S. Application Data

(62) Division of application No. 12/752,188, filed on Apr. 1, 2010, now Pat. No. 8,507,270.

(30) Foreign Application Priority Data

Jul. 27, 2009 (JP) ................................ 2009-174234

(51) Int. Cl.
*C12N 15/63* (2006.01)
*A61K 47/48* (2006.01)
*B82Y 5/00* (2011.01)
*C12N 15/87* (2006.01)

(52) U.S. Cl.
CPC .......... *C12N 15/63* (2013.01); *A61K 47/48346* (2013.01); *B82Y 5/00* (2013.01); *C12N 15/87* (2013.01)

(58) Field of Classification Search
None
See application file for complete search history.

(56) References Cited

U.S. PATENT DOCUMENTS

2008/0248281 A1* 10/2008 Nakaguma et al. ........ 428/312.8
2011/0020927 A1 1/2011 Yamaguchi et al.

FOREIGN PATENT DOCUMENTS

JP 2004-121041 A 4/2004

OTHER PUBLICATIONS

Boussif et al., "A versatile vector for gene and oligonucleotide transfer into cells in culture and in vivo: Polyethylenimine," Proc. Natl. Acad. Sci. USA, vol. 92, Aug. 1995, pp. 7297-7301.
Abdallah et al., "A Powerful Nonviral Vector for in Vivo Gene Transfer into the Adult Mammalian Brain: Polyethylenimine," Human Gene Therapy, vol. 7, Oct. 20, 1996, pp. 1947-1954.
Goula et al., "Size, diffusibility and transfection performance of linear PEI/DNA complexes in the mouse central nervous system," Gene Therapy, vol. 5, 1998, pp. 712-717.

(Continued)

*Primary Examiner* — Anna Pagonakis
(74) *Attorney, Agent, or Firm* — Kilyk & Bowersox, P.L.L.C.

(57) ABSTRACT

An object of the present invention is to achieve a method capable of increasing transfection efficiency of polyethyleneimine (PEI) and reducing toxicity thereof, to provide a PEI with high transfection efficiency, and to provide a method of introducing nucleic acids into cells comprising using the PEI. There are provided a method of introducing nucleic acids into cells comprising mixing acidified PEI with nucleic acids under acidic conditions and applying the resulting mixture to cells, a reagent for introducing nucleic acids into cells comprising an acidified PEI solution, and a reagent kit including the solution.

12 Claims, 7 Drawing Sheets

(56) References Cited

OTHER PUBLICATIONS

Zanta et al., "In Vitro Gene Delivery to Hepatocytes with Galactosylated Polyethylenimine," Bioconjugate Chem., vol. 8, 1997, pp. 839-844.
Fischer et al., "A Novel Non-Viral Vector for DNA Delivery Based on Low Molecular Weight, Branched Polyethylenimine: Effect of Molecular Weight on Transfection Efficiency and Cytotoxicity," Pharmaceutical Research, vol. 16, No. 8, 1999, pp. 1273-1279.
Ogris et al., "PEGylated DNA/transferrin-PEI complexes: reduced interaction with blood components, extended circulation in blood and potential for systemic gene delivery," Gene Therapy, vol. 6, 1999, pp. 595-605.
Wightman et al., "Different behavior of branched and linear polyethylenimine for gene delivery in vitro and in vivo," The Journal of Gene Medicine, vol. 3, 2001, pp. 362-372.
Durocher et al., "High-level and high-throughput recombinant protein production by transient transfection of suspension-growing human 293-EBNA1 cells," Nucleic Acids Research, vol. 30, No. 2, 2002, e9 (9 pages).
Brissault et al., "Synthesis of Linear Polyethylenimine Derivatives for DNA Transfection," Bioconjugate Chem., vol. 14, 2003, pp. 581-587.
Thomas et al., "Full deacylation of polyethylenimine dramatically boosts its gene delivery efficiency and specificity to mouse lung," Proc. Natl. Acad, Sci. USA, vol. 102, No. 16, Apr. 19, 2005, pp. 5679-5684.
Ogris et al., "The size of DNA/transferrin-PEI complexes is an important factor for gene expression in cultured cells," Gene Therapy, vol. 5, 1998, pp. 1425-1433.
Tseng et al., "Trehalose Enchances Transgene Expression Mediated by DNA-PEI Complexes," Biotechnol. Prog., vol. 23, 2007, pp. 1297-1304.
Pham et al., "Large-Scale Transient Transfection of Serum-Free Suspension-Growing HEK293 EBNA1 Cells: Peptone Additives Improve Cell Growth and Transfection Efficiency," Biotechnol. Bioeng., vol. 84, 2003, pp. 332-342.
Ehrhardt et al., "Polyethylenimine, a cost-effective transfection reagent," Signal Transduction, vol. 6, 2006, pp. 179-184.
Suh et al., "Ionization of Poly(ethylenimine) and Poly(allylamine) at Various pH's," Bioorganic Chemistry, vol. 22, 1994, pp. 318-327.
Clamme et al., "Monitoring of the Formation and Dissociation of Polyethylenimine/DNA Complexes by Two Photon Fluorescence Correlation Spectroscopy," Biophysical Journal, vol. 84, Mar. 2003, pp. 1960-1968.
Menzel et al., "Chemical properties of polyamines with relevance to the biomineralization of silica," Chem. Commun., 2003, pp. 2994-2995.
Godbey et al., "Poly(ethylenimine)-mediated gene delivery affects endothelial cell function and viability," Biomaterials, vol. 22, 2001, pp. 471-480.
Moghimi et al., "A Two-Stage Poly(ethylenimine)-Mediated Cytotoxicity: Implications for Gene Transfer/Therapy," Molecular Therapy, vol. 11, No. 6, Jun. 2005, pp. 990-995.
Ferrari et al., "ExGen 500 is an efficient vector for gene delivery to lung epithelial cells in vitro and in vivo," Gene Therapy, vol. 4, 1997, pp. 1100-1106.
Ira et al., "DNA Vector Polyethyleneimine Affects Cell pH and Membrane Potential: A Time-Resolved Fluorescence Microscopy Study," Journal of Fluorescence, vol. 13, No. 4, Jul. 2003, pp. 339-347.
Aldrich Catalog #343102 0.2 N HCl solution MSDS, 2012 (6 pages).
Hobel et al., "Polyethylenimine PEI F25-LMW allows the long-term storage of frozen complexes as fully active reagents in siRNA-mediated gene targeting and DNA delivery," European Journal of Pharmaceutics and Biopharmaceutics (2008), vol. 70, pp. 29-41, Elsevier.
Bertschinger et al., "Disassembly of polyethylenimine-DNA particles in vitro: Implications for polyethylenimine-mediated DNA delivery," Journal of Controlled Release (2006), vol. 116, pp. 96-104, Elsevier.
Devitt et al., "Optimized protocol for the large scale production of HIV pseudovirions by transient transfection of HEK293T cells with linear fully deacylated polyethylenimine," Journal of Virological Methods (2007), vol. 146, pp. 298-304, Elsevier.

\* cited by examiner

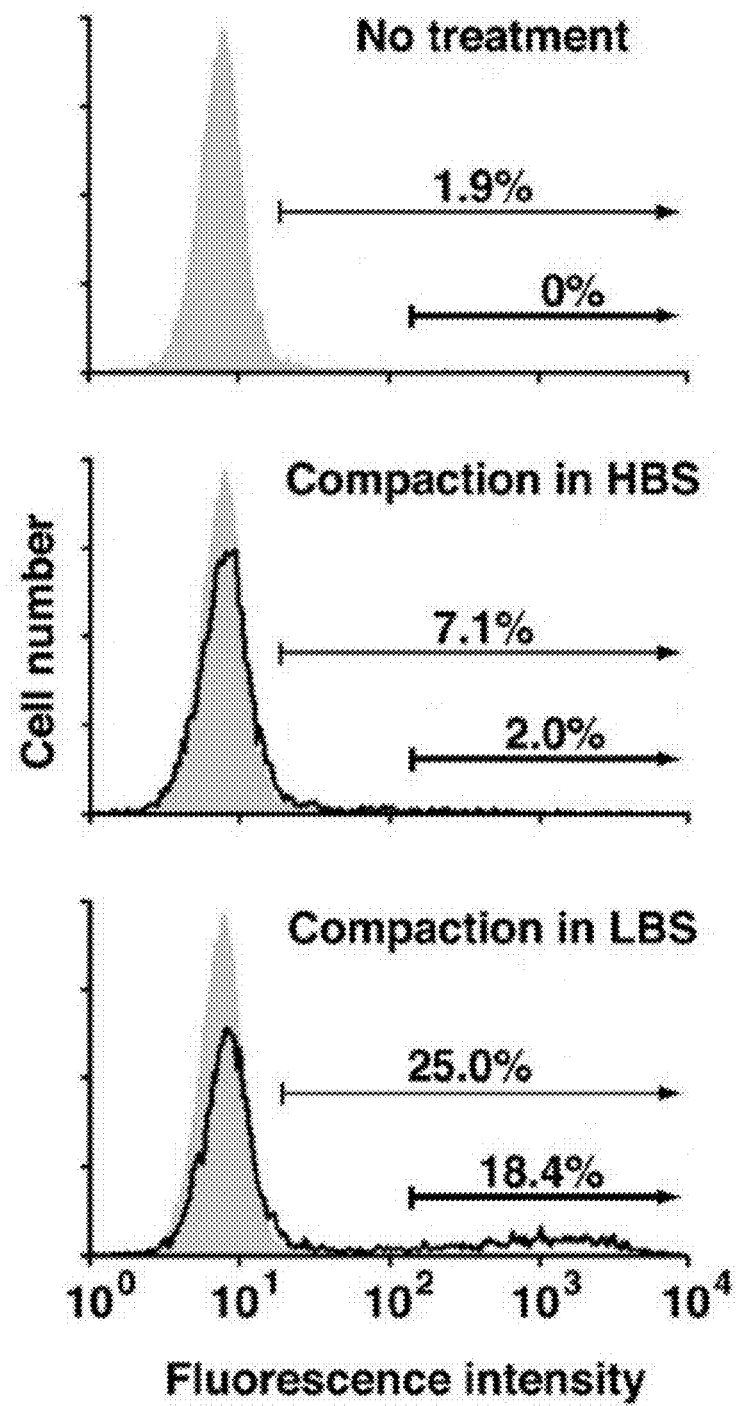
Figure 1-A

Figure 1-B
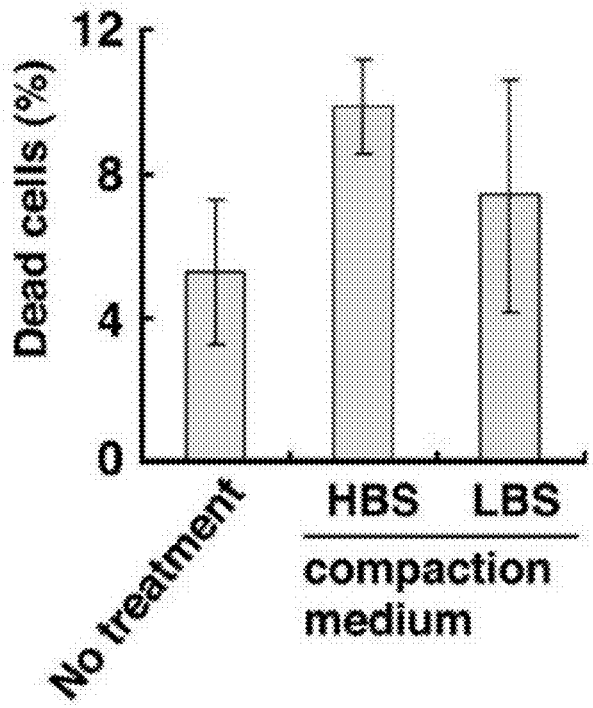
Figure 2-A
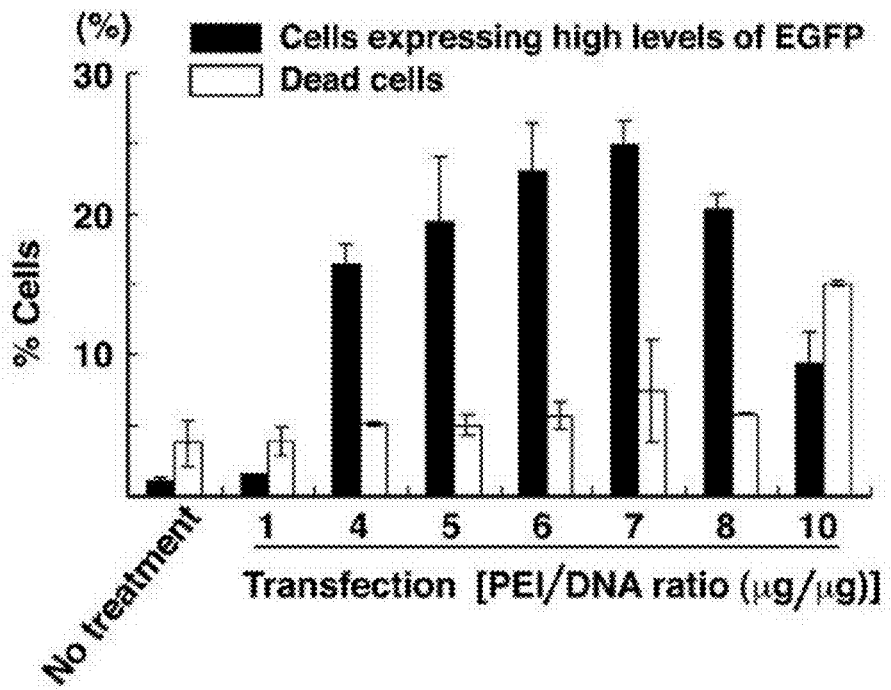

Figure 2-B
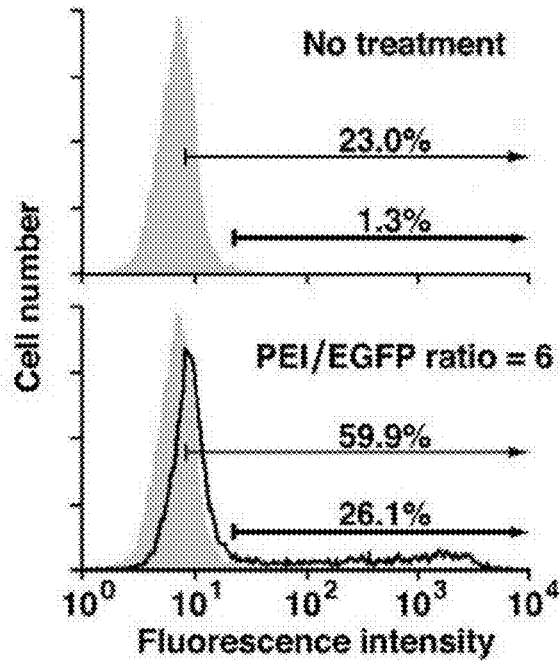
Figure 2-C
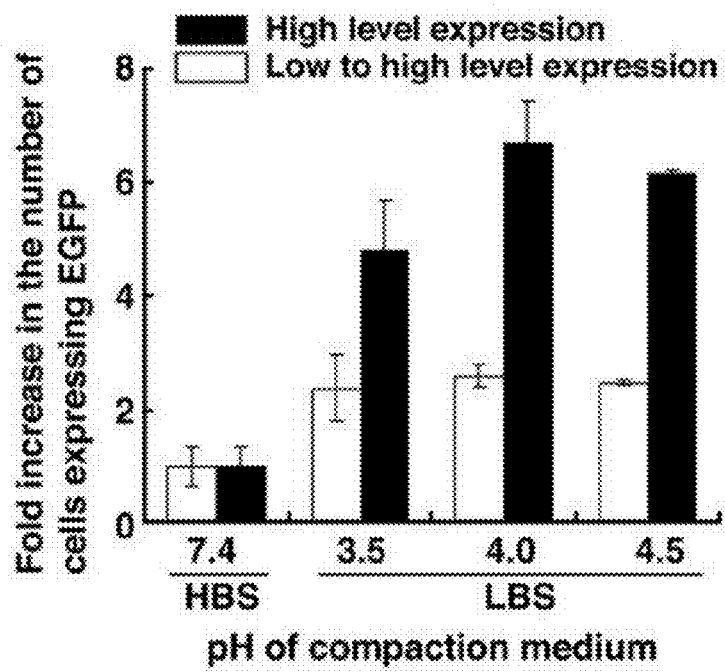

Figure 3-A
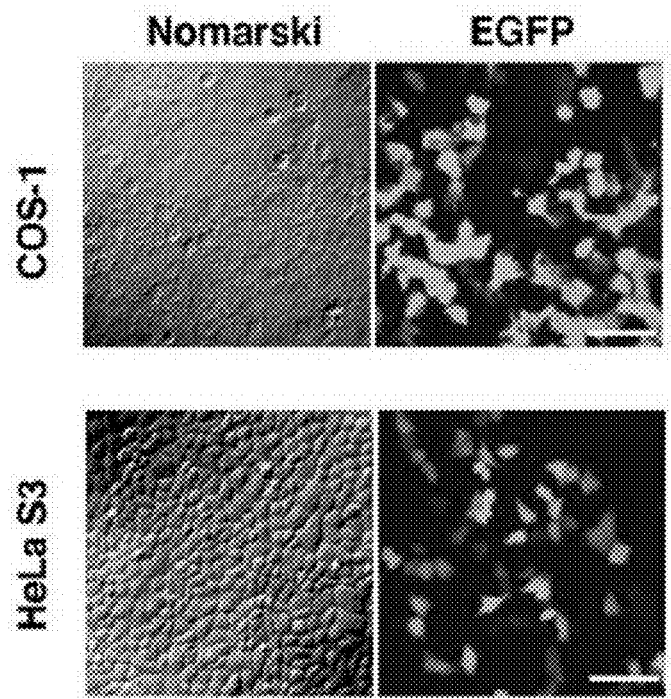
Figure 3-B
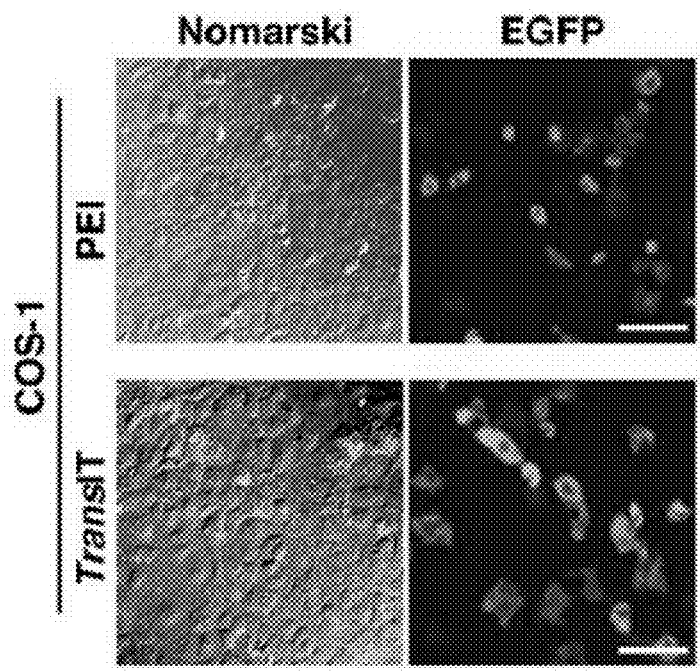

Figure 3-C
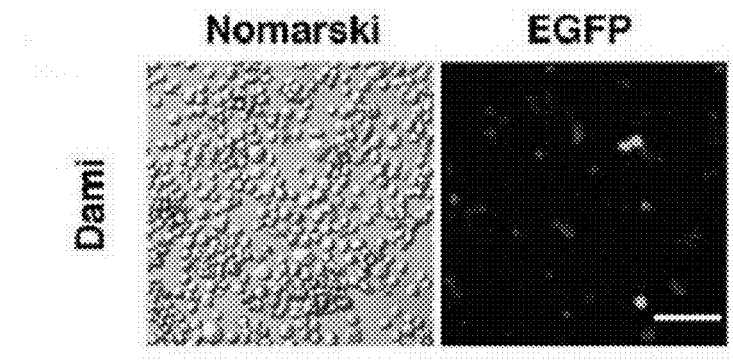
Figure 3-D
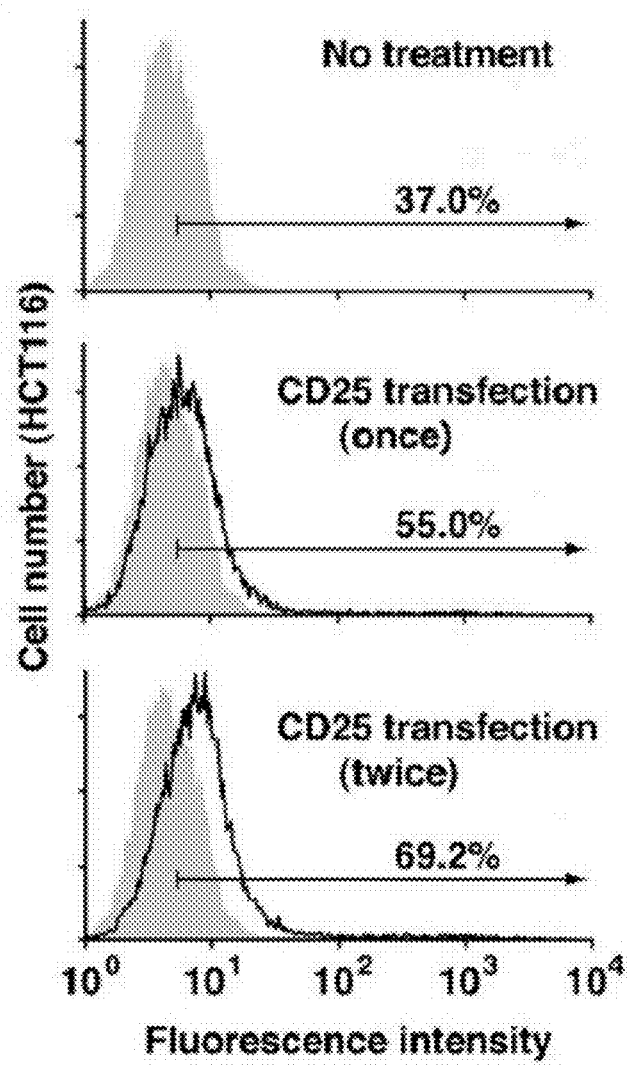

Figure 3-E
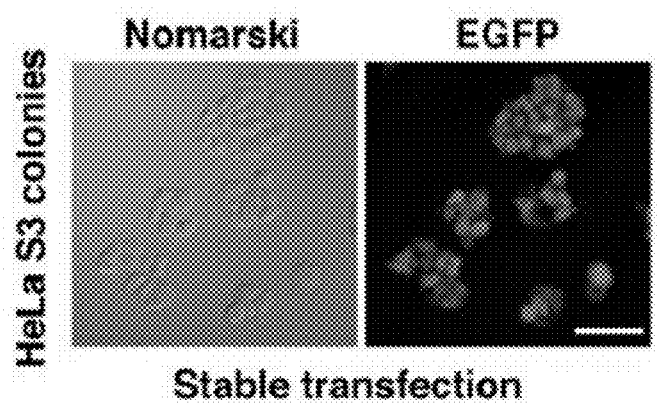

Figure 4

Example of a stock solution

1. PEI: 5mg/mL PEI (linear polyethyleneimine of a molecular weight 25,000) contained in 0.2N HCl
   - Dissolve PEI Powder in 0.2 N HCl immediately after purchase
   - Not neutralize the resulting solution
   - Store at 4°C or -80°C
2. LBS: 20 mM sodium lactate, pH 4.0 and 150 mM NaCl (compaction medium)
3. Plasmid DNA-containing TE (10mM Tris-HCl, pH8.0 and 1mM EDTA)
4. Serum-free medium
5. Serum-containing medium

Example of a transfection method

Step1: cell preparation

- Seed cells into 35-mm dishes at $1 \times 10^5$ cells per dish and culture them in serum-containing medium until 70-80% confluent
- Replace the culture medium with fresh serum-containing medium before transfection Step2: PEI/DNA polyplex formation (DNA compaction)

- Dilute 5 µg or 1 µg of plasmid DNA in 50 µl of LBS (solution A)
- Dilute 25 µg or 5 µg of PEI in 50 µl of LBS (solution B)
- Mix solution A with solution B at a PEI/DNA ratio of 5 (µg/µg) with gently mixing on a vortex, and allow the mixture to stand at room temperature for 20 minutes Step3: addition of PEI/DNA polyplex

- Dilute 100 µL of PEI/DNA polyplex in 500 µl of pre-warmed serum-free medium
- Add the diluted polyplex to cells in a dropwise manner
- Incubate the cells at 37°C Step4: removal of the transfection reagents to minimize toxicity

- Replace the culture medium with fresh serum-containing medium after 8-12 hours of incubation with PEI/DNA polyplex
- Culture the cells to express proteins, and passage them according to the needs

REAGENT KIT HAVING ACIDIFIED POLYETHVLENDIMINE FOR INTRODUCING NUCLEIC ACIDS INTO CELLS

This application is a divisional of U.S. patent application Ser. No. 12/752,188, filed Apr. 1, 2010, which claims priority to JP 2009-174234 filed Jul. 27, 2009.

TECHNICAL FIELD

The present method relates to a method of introducing nucleic acids into cells comprising using acidified polyethyleneimine. More specifically, the present invention relates to a method of introducing nucleic acids into cells comprising mixing polyethyleneimine with nucleic acids under acidic conditions and applying the resulting mixture to cells. Further, the present invention relates to a reagent for introducing nucleic acids into cells comprising an acidified polyethyleneimine solution and to a reagent kit including the solution.

BACKGROUND ART

The delivery of nucleic acids into cells is indispensable for basic research in molecular and cell biology as well as medical applications such as gene therapy. For example, a transfection method utilizing viral vectors and a non-viral transfection method are known as a method for introducing genes into cells.

A transfection method utilizing viral vectors gives high level of gene delivery. Viral vectors are efficient carriers for gene delivery, but their use is limited by the induction of immune responses and virus-associated pathogenicity.

A non-viral transfection method does not have such problems that are found in a transfection method utilizing viral vectors and thus has the potential to produce pharmaceuticals from nucleic acids (Non-Patent Document 1). According to the non-viral transfection method, the products should be capable of being produced in large quantities with high reproducibility and acceptable cost, and stable to storage.

There are many known non-viral transfection methods including the major methods that use cationic lipids and/or cationic polymers. A series of non-viral transfection reagents containing cationic lipids or cationic polymers as main ingredients are now commercially available and provided for use. However, the transfection methods using such reagents have a problem in that the nucleic acids incorporated into cells through endocytosis are largely degraded in lysosomes resulting in low transfection efficiency. In addition, many of the commercially available transfection reagents are quite expensive at the present time, and their high costs are obstacles to experimentation with a large number and/or large scales of transfection.

The cationic polymer polyethylenimine (hereinafter, abbreviated as PEI) is an inexpensive, non-viral and non-liposomal reagent for transfection and is known to be one of the most cost-effective vehicles. PEI has a high cationic charge density potential and efficiently condenses DNA (compaction) to form stable complexes termed polyplexes that are incorporated into cells through endocytosis. Thus, an efficient transfection is achieves by using PEI (Non-Patent Document 2). In addition, PEI has a high pH-buffering capacity, leading to protection of incorporated DNA from lysosomal degradation and its efficient release from lysosomes into the cytoplasm. PEI is therefore useful for a transfection reagent, and is used to transfect mammalian cells with DNA in vitro and in vivo (Non-Patent Documents 2-4).

However, a transfection method using PEI has some problems such as unignorable degrees of toxicity and considerable deterioration in transfection efficiency due to low stability of PEI.

In order to improve transfection efficiency, extensive studies have been performed on the size, structure and chemical modification of PEI (Non-Patent Documents 4-11), and addition of supplements to a PEI/DNA polyplex or compacted DNA was also examined (Non-Patent Documents 12-13).

PRIOR ARTS

Patent Documents

Patent Document 1: Tokuhyo 2008-509076.
Patent Document 2: Tokuhyo 2006-516259.

Non-Patent Documents

Non-Patent Document 1: Davis, M. E. (2002) Non-viral gene delivery systems. Curr. Opin. Biotechnol. 13, 128-131.
Non-Patent Document 2: Boussif, O. et al., (1995) A versatile vector for gene and oligonucleotide transfer into cells in culture and in vivo: Polyethylenimine. Proc. Natl. Acad. Sci. USA 92, 7297-7301.
Non-Patent Document 3: Abdallah, B. et al., (1996) A powerful nonviral vector for in vivo gene transfer into the adult mammalian brain: Polyethylenimine. Hum. Gene Ther. 7, 1947-1954.
Non-Patent Document 4: Goula, D. et al., (1998) Size, diffusibility and transfection performance of linear PEI/DNA complexes in the mouse central nervous system. Gene Ther. 5, 712-717.
Non-Patent Document 5: Zanta, M. A. et al., (1997) In vitro gene delivery to hepatocytes with galactosylated polyethylenimine. Bioconjug. Chem. 8, 839-844.
Non-Patent Document 6: Fischer, D. et al., (1999) A novel non-viral vector for DNA delivery based on low molecular weight, branched polyethylenimine: Effect of molecular weight on transfection efficiency and cytotoxicity. Pharm. Res. 16, 1273-1279.
Non-Patent Document 7: Ogris, M. et al., (1999) PEGylated DNA/transferrin-PEI complexes: Reduced interaction with blood components, extended circulation in blood and potential for systemic gene delivery. Gene Ther. 6, 595-605.
Non-Patent Document 8: Wightman, L. et al., (2001) Different behavior of branched and linear polyethylenimine for gene delivery in vitro and in vivo. J. Gene Med. 3, 362-372.
Non-Patent Document 9: Durocher, Y. et al., (2002) High-level and high-throughput recombinant protein production by transient transfection of suspension-growing human 293-EBNA1 cells. Nucleic Acids Res. 30, e9.
Non-Patent Document 10: Brissault, B. et al., (2003) Synthesis of linear polyethylenimine derivatives for DNA transfection. Bioconjug. Chem. 14, 581-587.
Non-Patent Document 11: Thomas, M. et al., (2005) Full deacylation of polyethylenimine dramatically boosts its gene delivery efficiency and specificity to mouse lung. Proc. Natl. Acad. Sci. USA 102, 5679-5684.
Non-Patent Document 12: Ogris, M. et al., (1998) The size of DNA/transferring-PEI complexes is an important factor for gene expression in cultured cells. Gene Ther. 5, 1425-1433.
Non-Patent Document 13: Tseng, W. C. et al., (2007) Trehalose enhances transgene expression mediated by DNA-PEI complexes. Biotechnol. Prog. 23, 1297-1304.

DISCLOSURE OF THE INVENTION

Problem to be Solved by the Invention

Extensive studies have been performed with focusing on the size, structure and chemical modification of PEI in order to improve transfection efficiency. However, increased transfection efficiency of PEI and reduced toxicity thereof are not yet achieved.

An object of the present invention is to achieve a method capable of increasing transfection efficiency of PEI and reducing toxicity thereof, to provide a PEI with high transfection efficiency, and to provide a method of introducing nucleic acids into cells comprising using the PEI.

Means for Solving the Object

The present inventors diligently conducted various researches to achieve the foregoing objects. In the researches, conditions of PEI solution and polyplex formation as well as transfection time were studied to resolve the defects of PEI. As a result, it was found that acidified PEI and polyplex formation under acidic conditions ensure high transfection efficiency. Further, it was found that elimination of PEI after transfection results in sufficient transfection efficiency and reduced toxicity. The present inventors thus accomplished the present invention on the basis of these findings.

More precisely, the present invention relates to the followings:

1. A method of introducing nucleic acids into cells, comprising steps of:
    (1) a step of mixing polyethyleneimine (PEI) with nucleic acids under acidic conditions of pH from 3.5 to 4.5, and
    (2) a step of applying the resulting mixture to cells,
2. The method of introducing nucleic acids into cells according to the above 1, further comprising the following step after the step (2):
    (3) a step of replacing cell culture medium with fresh culture medium,
3. The method of introducing nucleic acids into cells according to the above 1 or 2, wherein the PEI is linear PEI,
4. The method of introducing nucleic acids into cells according to the above 1 or 2, wherein the PEI is linear PEI with a molecular weight of approximately 25,000,
5. The method of introducing nucleic acids into cells according to any one of the above 1 to 4, wherein a weight ratio of the PEI to the nucleic acids is from 4:1 to 8:1,
6. The method of introducing nucleic acids into cells according to any one of the above 1 to 5, wherein the PEI described in any one of the above 1 to 5 is a solution (PEI solution) of pH from 0.5 to 2.0,
7. The method of introducing nucleic acids into cells according to any one of the above 1 to 5, wherein the PEI described in any one of the above 1 to 5 is a hydrochloric acid solution of PEI,
8. The method of introducing nucleic acids into cells according to any one of the above 1 to 5, wherein the PEI described in any one of the above 1 to 5 is a PEI solution prepared by dissolving PEI in a 0.2N hydrochloric acid solution,
9. A method of introducing nucleic acids into cells, comprising steps of:
    (1) a step of mixing polyethyleneimine (PEI) with nucleic acids under acidic conditions of pH from 3.5 to 4.5, and
    (2) a step of applying the resulting mixture to cells, and
    (3) a step of replacing cell culture medium to fresh culture medium, wherein the PEI is a PEI solution prepared by dissolving linear PEI with a molecular weight of approximately 25,000 in a 0.2N hydrochloric acid solution, and a weight ratio of the PEI to the nucleic acids is from 4:1 to 8:1,
10. A reagent kit for introducing nucleic acids into cells, comprising a polyethyleneimine (PEI) solution, wherein the PEI solution is of pH from 0.5 to 2.0,
11. The reagent kit for introducing nucleic acids into cells according to the above 10, wherein the PEI solution is a hydrochloric acid solution of PEI,
12. The reagent kit for introducing nucleic acids into cells according to the above 10, wherein the PEI solution is a PEI solution prepared by dissolving PEI in a 0.2N hydrochloric acid solution,
13. The reagent kit for introducing nucleic acids into cells according to any one of the above 10 to 12, wherein PEI being contained in the PEI solution is linear PEI,
14. The reagent kit for introducing nucleic acids into cells according to any one of the above 10 to 12, wherein PEI being contained in the PEI solution is linear PEI with a molecular weight of approximately 25,000,
15. A reagent kit for introducing nucleic acids into cells, comprising a polyethyleneimine (PEI) solution, wherein the PEI solution is a PEI solution prepared by dissolving linear PEI with a molecular weight of approximately 25,000 in a 0.2N hydrochloric acid solution,
16. A reagent kit for introducing nucleic acids into cells, comprising a polyethyleneimine (PEI) solution, wherein the PEI solution is of pH from 0.5 to 2.0, and maintains efficiency in introducing nucleic acids into cells.

Advantages of the Invention

The present invention can provide a method of introducing nucleic acids into cells, comprising mixing PEI with nucleic acids under acidic conditions and applying the resulting mixture to cells.

Further, the present invention can provide a reagent for introducing nucleic acids into cells comprising an acidified PEI solution, and a reagent kit for introducing nucleic acids into cells comprising the solution.

The method of introducing nucleic acids into cells according to the present invention can ensure high transfection efficiency and minimum toxicity in introducing nucleic acids into various kinds of cells and cultured cells. In addition, the cost required for the present method of nucleic acid introduction can be considerably lowered to approximately 1:10,000 compared to that required for a method of nucleic acid introduction using various commercially available reagents.

Further, the acidified PEI solution retains transfection activity of PEI during long time storage compared to a neutral PEI solution, which allows the efficiency of nucleic acid introduction into cells to be maintained.

Thus, the present invention achieves nucleic acid introduction into cells in a simple and cost effective manner with high efficiency.

BRIEF DESCRIPTION OF THE DRAWINGS

FIG. 1-A shows that PEI-induced DNA compaction in acidic conditions resulted in increased efficiency of PEI/DNA polyplex-mediated transfection. EGFP expression vector and PEI were mixed in HBS (pH 7.4) or LBS (pH 3.5) to induce DNA compaction (in the Figure, represented as Compaction in HBS or Compaction in LBS). The resulting PEI/DNA polyplex was transiently transfected into HeLa cells. EGFP expression in the cells was analyzed by flow cytometry. Non-treated cells were analyzed in the same manner (in the Figure, represented as No treatment). The longitudinal axis of the figure represents number of cells (Cell number) and the transverse axis represents Fluorescence intensity. In addition, shaded areas in the figure show histograms of non-treated cells and solid line areas show histograms of treated cells. Efficiencies of the transient transfection were quantitated by counting the number of cells expressing EGFP at high levels (thick arrows) and at low to high levels (thin arrows). (Example 1)

FIG. 1-B shows that PEI-induced DNA compaction in acidic conditions resulted in reduced cytotoxicity in PEI/DNA polyplex-mediated transfection. Transfection was carried out as shown in the description for FIG. 1-A, and then the transfected HeLa cells were stained with PI and analyzed for PI-stained dead cells by flow cytometry. Data represent means±S.D. (n=3). The longitudinal axis of the figure represents ratio of Dead cells (%). (Example 1)

FIG. 2-A shows results of a study examining effects of PEI/DNA ratios and pH during DNA compaction on transfection efficiency. PEI and EGFP expression vector were mixed in LBS (pH 3.5) at various PEI/DNA ratios, and the resulting PEI/DNA polyplex was transiently transfected into HeLa cells. EGFP expression and toxicity were analyzed by flow cytometry. Non-treated cells were analyzed in the same manner (in the Figure, represented as No treatment). The longitudinal axis of the figure represents ratio of cells (%). The numerical values shown in the figure represents PEI/DNA ratio at the time when preparing PEI/DNA polyplex used for transfection (Transfection [PEI/DNA ratio (μg/μg)]). In the Figure, filled bars represent cells expressing high levels of EGFP and open bars represent dead cells. (Example 2)

FIG. 2-B shows results of a study examining effects of PEI/DNA ratios and pH during DNA compaction on transfection efficiency. PEI and EGFP expression vector were mixed in LBS (pH 3.5) at a ratio of 6 (μg/μg) (in the figure, represented as PE/EGFP ratio=6), and the resulting PEI/DNA polyplex was transiently transfected into HeLa cells. EGFP expression was analyzed by flow cytometry. Non-treated cells were analyzed in the same manner (in the Figure, represented as No treatment). The longitudinal axis of the figure represents number of cells (Cell number), and the transverse axis represents Fluorescence intensity. In addition, shaded areas in the figure show histograms of non-treated cells and solid line areas show histograms of transfected cells. Efficiencies of the transient transfection were quantitated by counting the number of cells expressing EGFP at high levels (thick arrows) and at low to high levels (thin arrows). (Example 2)

FIG. 2-C shows results of a study examining effect of pH during DNA compaction on transfection efficiency. PEI and EGFP expression vector were mixed at a ratio of 5 (μg/μg) in HBS (pH 7.4) or LBS (pH 3.5, 4.0, 4.5), and the resulting PEI/DNA polyplex was transiently transfected into HeLa cells. The longitudinal axis of the figure represents fold increase in the number of cells expressing EGFP. The numerical values shown in the figure represents pH of DNA compaction medium. In the Figure, filled bars and open bars respectively represent cells expressing high levels of EGFP (represented as High level expression) and cells expressing low to high levels of EGFP (represented as Low to High level expression). Data represent means±S.D. (n=3) (Example 2)

FIG. 3-A shows results of transfection using PEI/DNA polyplex prepared under acidic conditions into COS-1, HeLa S3, Dami, and HCT116 cells. EGFP expression was analyzed by fluorescence microscopy. The cells were transiently transfected with the polyplex formed by mixing 5 μg of EGFP expression vector with 25 μg of PEI in LBS (pH 4.0), and after 12 hours of culture the medium was replaced with fresh serum-containing medium. Then, cell morphology and EGFP expression were observed under a Nomarski differential interference contrast microscope and a fluorescence microscope. Scale bars, 10 μm. (Example 3)

FIG. 3-B shows results of a study comparing transfection of COS-1 cells using PEI/DNA polyplex prepared under acidic condition and transfection thereof using an optimum dose of TransIT-LT1. The cells were transiently transfected with the polyplex formed by mixing 1 μg of EGFP expression vector with 5 μg of PEI in LBS (pH 4.0), or an optimum dose of TransIT-LT1. Then, cell morphology and EGFP expression were observed under a Nomarski differential interference contrast microscope and a fluorescence microscope. Scale bars, 10 μm. (Example 3)

FIG. 3-C shows results of transfection of Dami cells in suspension culture using PEI/DNA polyplex prepared under acidic conditions. Dami cells in suspension culture were attached to culture dishes, and transiently transfected with the polyplex formed by mixing 4 μg of EGFP expression vector with 26 μg of PEI in LBS (pH 4.0). Then, cell morphology and EGFP expression were observed under a Nomarski differential interference contrast microscope and a fluorescence microscope. Scale bars, 10 μm. (Example 3)

FIG. 3-D shows successful transfection of HCT116 cells, which are highly sensitive to PEI exposure leading to cell aggregation and cell death, using PEI/DNA polyplex prepared under acidic conditions. The cells were transiently transfected once or twice with the polyplex formed by mixing 6 μg of CD25 expression vector with 7.5 μg of PEI in LBS (pH 4.0) (in the figure, represented as CD25 transfection (once) or CD25 transfection (twice)), and stained with anti-CD25 antibody followed by analyzing CD25 expression using a cell sorter. Non-treated cells were analyzed in the same manner (in the Figure, represented as No treatment). The longitudinal axis of the figure represents number of HCT 116 cells (Cell number (HCT116)), and the transverse axis represents Fluorescence intensity. In addition, shaded areas in the figure show histograms of non-treated cells and solid line areas show histograms of transfected cells. Efficiencies of the transfection were quantitated by counting the number of cells expressing CD25 at low to high levels (thin arrows). (Example 3)

FIG. 3-E shows results of producing stably transfected cell clones by using PEI/DNA polyplex obtained in acidic conditions. HeLa S3 cells were stably transfected with the polyplex formed by mixing EGFP expression vector with PEI in LBS (in the figure, represented as Stable transfection). Then, zeocin-resistant colonies were cloned in 2 weeks (in the figure, represented as HeLa S3 colonies) and observed for cell morphology and EGFP expression under a Nomarski differential interference contrast microscope and a fluorescence microscope. Scale bar, 10 μm.

FIG. 4 shows a specific example of a method of nucleic acids introduction into cells using acidified PEI.

DETAILED DESCRIPTION OF THE INVENTION

The present invention relates to a method of introducing nucleic acids into cells comprising using PEI. The method according to the present invention is characterized by comprising the steps of mixing PEI with nucleic acids under acidic conditions and applying the resulting mixture to cells.

Further, the present invention relates to a reagent for introducing nucleic acids into cells comprising an acidified PEI solution, and a reagent kit for introducing nucleic acids into cells comprising the solution. The PEI solution according to the present invention is characterized in that it is dissolved in an acidic solvent.

The term "nucleic acid" means a chain-like polynucleotide, which comprises a nucleotide as a fundamental unit that is constituted of a purin or pyrimidine base, a sugar and a phosphoric acid, wherein the phosphoric acid forms a diester bond between sugars in different nucleotides at the carbon at 3'position and the carbon at 5'position for polymerization. The nucleic acid is largely classified by difference of the sugar into a deoxyribonucleic acid (DNA) where sugar is deoxyribose and a ribonucleic acid (RNA) where sugar is ribose.

The term "nucleic acid" includes a gene, a DNA, a RNA, an oligonucleotide, and a polynucleotide. Further, the term "nucleic acid" can be exchangeably used herein with a gene, a DNA, a RNA, an oligonucleotide, and a polynucleotide.

The phrase "introducing nucleic acids into cells" can be exchangeably used herein with a phrase "transfection of cells".

The term "cells" include isolated cells, cells contained in tissues isolated from organisms, and cultured cells. The isolated cells and the cultured cells can be adherent cells or suspension cells.

PEI is a cationic polymer and is efficient for DNA compaction to form stable complex termed polyplex. The polyplex are incorporated into cells through endocytosis. Thus, an efficient transfection is achieves by using PEI (Non-patent reference 2).

PEI can be linear PEI or branched PEI, where linear PEI is preferably used. Linear PEI has a higher transfection efficiency compared to branched PEI. In respect to the transfection efficiency, PEI with a molecular weight of from 10,000 to 800,000 Da, preferably from 10,000 to 50,000 Da, more preferably from 10,000 to 25,000 Da, further preferably approximately 25,000 Da can be available for use. Specifically, linear PEI with a molecular weight of approximately 25,000 Da is preferably used. In addition, chemically modified linear PEI or branched PEI can be also used. PEI is commercially available and easily obtainable. For example, PEI produced by Polysciences, Inc. (Warrington, Pa., USA) can be preferably used.

PEI is preferably to be an acidified PEI solution. The term "acidified PEI solution" herein means a PEI solution that is prepared by dissolving PEI in an acidic solvent. Meanwhile, the term "neutralized PEI solution" means a PEI solution that is prepared by dissolving PEI in a neutral solvent. Acidity of the acidified PEI solution is preferably pH from 0 to 2.0, more preferably pH from 0.5 to 2.0. Acidity out of this range gives reduced transfection activity of PEI. Any of acidic solvents can be used as far as being capable of maintaining acidity of a PEI solution within an aforementioned range and not affecting the transfection activity of PEI. Examples of the acidic solvent include mineral acids such as Hydrochloric acid (hereinafter, may be abbreviated as HCl), and organic acids with pH in acidic range such as glycine-hydrochloric acid solution. More specifically, the acidic solvent is exemplified by 0.01N to 1N aqueous hydrochloric acid solution, and preferably by 0.2N aqueous hydrochloric acid solution.

Preparation of the acidic PEI solution is performed immediately after purchase of PEI power by dissolving it in an acidic solvent. Since PEI is easily oxidized by air, it is unstable even if it is in powered form and its transfection activity is reduced during storage in powdered form at −80° C. once the bottle is opened. Therefore, it is preferable to dissolve purchased PEI power in an acidic solvent immediately after the bottle is opened. In order to maintain stability during storage, it is preferable to dissolve PEI in an acidic solvent at a concentration of more than 1 mg/ml.

A large number of papers has already been reported describing successful transfection with neutralized PEI solution (Non-Patent Document 2, Non-Patent Document 6, Non-Patent Document 12, Pham, P. L. et al., (2003) Large-scale transient transfection of serum-free suspension-growing HEK293 EBNA1 cells: Peptone additives improve cell growth and transfection efficiency. Biotechnol. Bioeng. 84, 332-342, hrhardt, C. et al., (2006) Polyethylenimine, a cost-effective transfection reagent. Signal Transduction 6, 179-184).

Actually indeed, an unpredictable decrease in the transfection activity of PEI is often observed when using PEI. Thus, the neutralized PEI solution is suspected to be unstable.

The acidified PEI solution, on the other hand, preserved almost full transfection activity after long-term storage. Specifically, dissolving PEI in 0.2N HCl resulting in being pH of about 1 preserved the full transfection activity for at least six months during storage at 4° C. or −80° C. More specifically, the transfection activity was maximal immediately after preparation, and was preserved after six months' storage without any loss of activity. On the contrary, when PEI was dissolved in HBS (pH 7.4), transfection activity was severely decreased during one-month storage at 4° C. or −80°. Specifically, taking the transfection activity immediately after preparation as 100%, the activity was 0% after one-month storage, thus was completely lost. In addition, dissolving PEI in ethanol drastically decreased its transfection activity within a couple of weeks during storage at 4° C. Specifically, taking the transfection activity at the time of preparation as 100%, the activity was 0% after a couple of weeks' storage, thus was completely lost.

The acidified PEI solution does not suffer from air oxidization because of protonation of the lone pairs on nitrogen atoms in all imino groups, which results in protection from reduction of transfection activity during storage.

The method of introducing nucleic acids into cells according to the present invention comprises mixing PEI with nucleic acids under acidic conditions and applying the resulting mixture to cells. Mixing PEI with nucleic acids results in PEI-induced efficient compaction of nucleic acids to form stable complexes termed polyplexes. Since polypexes are incorporated into cells through endocytosis, transfection can be efficiently achieved.

In the method of introducing nucleic acids into cells according to the present invention, the aforementioned acidified PEI solution is preferably used.

The phrase "under acidic conditions" means under conditions of pH3.2 to 4.5, preferably of pH4.0. Mixing PEI with nucleic acids can be carried out by, for example, adding both PEI and nucleic acid together in an acidic solvent. Alternatively, it can be carried out by, adding PEI and nucleic acid individually in acidic solvents followed by mixing the acidic solvents. Hereinafter, a medium used for nucleic acid compaction by mixing PEI with nucleic acids may be called a compaction medium. The compaction medium can be any buffer solution with pH 3.5 to 4.5 as far as it does not affect to cells. For example, lactate-buffered saline (LBS), acetate-buffered saline, and phosphate buffered saline can be used. More specifically, the compaction medium can be exemplified by lactate-buffered saline (LBS) with pH 4.0.

It is supposed that under conditions of pH3.5 to 4.5, preferably pH 4.0, PEI has a sufficient positive charge and phosphate group of nucleic acids has a negative charge, which leads to potent electric association between PEI and nucleic acids resulting in formation of compact polyplexes. Under neutral conditions, PEI has a reduced positive charge while nucleic acids have a sufficient negative charge. Under strong acidic conditions under pH3.5, nucleic acids do not have negative charge. Therefore, these conditions lead to insufficient polyplex formation. Without polyplex formation by compaction, nucleic acids are not incorporated into cells. In addition, if polyplexes are not compact ones, they are degraded by nuclease when they are incorporated into cells and transported to lysosomes. Therefore, Mixing PEI with nucleic acids is carried out under conditions of pH3.5 to 4.5, preferably pH4.0. Polyplexes formed by PEI and nucleic acids has a feature that they are efficiently released to the cytoplasm after being transported to lysosomes, and the released polyplexes are transported to nucleus. In the nucleus, nucleic acids are dissociated from polyplexes and revert to relaxed structure to exert their function.

Applying a mixture of PEI and nucleic acids to cells is carried out by adding the mixture to cell-containing solutions or solutions containing tissues isolated from organisms. Cells contained in cell-containing solutions can be adherent cells or suspension cells.

Cells are treated with a mixture of PEI and nucleic acids for a time period that is not limited as far as it is to be obtained high transfection efficiency, and can be determined by repeated simple experiments for optimization. In long time treatment, cells are affected by cytotoxicity of PEI resulting in an increased ratio of dead cells and thereby giving reduced transfection efficiency. Specifically, cells can be treated, for example, for a time period of preferably from 8 hours to 24 hours, more preferably from 8 hours to 12 hours, still more preferably 8 hours.

In order to avoid the cytotoxicity of PEI, it is preferable to replace culture medium to fresh culture medium when after treating cells with a mixture of PEI and nucleic acids. Culture medium replacement after transfection can minimize the cytotoxicity of PEI without any damage to the high transfection efficiency. It is conceivable that polyethyleneimine once incorporated in cells loses toxicity by metabolization if it is not a huge amount.

PEI and nucleic acids are mixed at a ration that is not limited as far as it is to be obtained high transfection efficiency, and can be determined by repeated simple experiments for optimization. It is conceivable that an optimum mixing ration varies according to a molecular weight of PEI. For example, in case of using PEI with a molecular weight of around 25,000 Da, PEI and nucleic acids are mixed preferably at a weight ration within a range from 4:1 to 8:1. A weight ratio out of the range gives reduced transfection activity of PEI. In addition, a weight ratio above 8:1 gives increased cytotoxicity due to an excess of PEI. When PEI is an acidified PEI solution, a weight ratio of PEI and nucleic acids is expressed as a weight ration of PEI contained in the acidic PEI solution and nucleic acids. Further, in case of using PEI with a molecular weight of around 25,000 Da for transfection of cells highly sensitive to toxicity of PEI, it is preferable to reduce a mixing ration of PEI and nucleic acids to an extent of 1.25:1 at most.

The method of introducing nucleic acids into cells according to the present invention preferably uses a PEI solution prepared by dissolving linear PEI with a molecular weight of approximately 25,000 in a 0.2N hydrochloric acid solution, and comprises the following steps:
(1) a step of mixing PEI with nucleic acids in a weight ratio ranging from 4:1 to 8:1 under acidic conditions of pH ranging from 3.5 to 4.5,
(2) a step of applying the resulting mixture to cells, and
(3) a step of replacing cell culture medium to fresh culture medium.

The method of introducing nucleic acids into cells according to the present invention is illustrated by a specific example shown in FIG. 4.

The method of introducing nucleic acids into cells according to the present invention can be employed in both transient introduction of nucleic acids into cells and stable introduction of nucleic acids into cells.

Further, the method of introducing nucleic acids into cells according to the present invention can be applied to cells that are easily affected by the cytotoxicity of PEI due to the high susceptibility to PEI. When transfecting such cells by the present method, high transfection efficiency can be achieved by treating cells plural times with a mixture of PEI and nucleic acids which mixing ratio is lowered than a standard ratio to reduce effect of the cytotoxicity of PEI.

Further, since many suspension culture cells in general are poorly transfected using chemical transfection reagents, electroporation is usually performed for introduction of nucleic acids. However, the present method can be applied to such suspension culture cells to achieve introduction of nucleic acids. The present method is useful in comparison to electroporation, since it does not require special equipment and can be performed for a small number of cells.

The method of introducing nucleic acids into cells according to the present invention showed transfection efficiency about 2 times to about 7 times higher and low cytotoxicity in comparison to a conventional method using neutralized PEI for introducing nucleic acids. In addition, the present method is low cost and cost-effective in comparison to a non-viral transfection method using other reagents.

The aforementioned acidified PEI solution can be used as a reagent for use in introducing nucleic acids into cells. More specifically, the present invention can provide a reagent for introducing nucleic acids into cells comprising a PEI solution, where the PEI solution is of pH from 0.5 to 2.0. Preferably, the reagent for introducing nucleic acids into cells according to the present invention comprises a PEI solution that is prepared by dissolving linear PEI with a molecular weight of approximately 25,000 in a 0.2N hydrochloric acid solution The aforementioned acidified PEI solution can be provided as a reagent kit including the solution in a form of individual package. More specifically, the present invention can provide a reagent kit for introducing nucleic acids into cells comprising a PEI solution, where the PEI solution is of pH from 0.5 to 2.0. Preferably, the reagent kit according to the present invention comprises a PEI solution that is prepared by dissolving linear PEI with a molecular weight of approximately 25,000 in a 0.2N hydrochloric acid solution. The present reagent kit can be preferably used in the method of introducing nucleic acids into cells according to the present invention.

As described above, acidification of PEI ensures long-term preservation of its transfection activity and achieves high transfection efficiency and minimal cytotoxicity in introduction of DNA into a wide variety of cell lines. Notably, the cost per test using acidified PEI is drastically reduced to approximately 1:10,000, compared with various commercial reagents. Thus, acidification of PEI accomplishes cost-effective, high-efficiency transfection.

Hereinafter, the present invention is described in particular with reference to examples, but it is not limited to the examples below.

Materials and methods used in the following examples are first described shortly.

Reagents and Plasmids

Linear PEI (MW 25,000) was purchased from Polysciences, Inc. PEI powder was dissolved in 0.2 N HCl at a concentration of 5 mg/ml, and aliquots were stored at 4° C. or −80° C. HEPES-buffered saline (hereinafter, may be abbreviated as HBS: 20 mM HEPES-KOH, pH 7.4, and 150 mM NaCl) and lactate-buffered saline (hereinafter, may be abbreviated as LBS: 20 mM sodium lactate, pH 3.5, 4.0 or 4.5, and 150 mM NaCl) were prepared. The TransIT-LT1 transfection reagent was purchased from Mirus Bio LLC. The vector pcDNA4-TO-EGFP that encodes enhanced green fluorescent protein (hereinafter, may be abbreviated as EGFP) was constructed using pcDNA4/TO vector (Invitrogen) by a method previously reported (Nakayama, Y. et al., (2006) Involvement of the N-terminal unique domain of Chk tyrosine kinase in Chk-induced tyrosine phosphorylation in the nucleus. Exp. Cell Res. 312, 2252-2263). The pCAG vector encoding CD25 (pCAG/TetR-IRES-CD25) was constructed by a method previously reported (Miyazaki, J. et al., (1989) Expression vector system based on the chicken beta-actin promoter directs efficient production of interleukin-5. Gene 79, 269-277).

Cell Lines

Human epithelial HeLa and HeLa S3 cells (Japanese Collection of Research Bioresources, Osaka) were cultured in Iscove's modified Dulbecco's medium (IMDM) supplemented with 5% fetal bovine serum (FBS) and with 5% bovine serum (BS), respectively. Human megakaryocytic Dami cells were maintained in suspension culture in IMDM supplemented with 10% horse serum, as described previously (Greenberg, S. M. et al., (1988) Characterization of a new megakaryocytic cell line: The Dami cell. Blood 72, 1968-1977; Hirao, A. et al., (1998) Overexpression of C-terminal Src kinase homologous kinase suppresses activation of Lyn tyrosine kinase required for VLA5-mediated Dami cell spreading. J. Biol. Chem. 273, 10004-10010; Sato, I. et al., (2009) Differential trafficking of Src, Lyn, Yes and Fyn is specified by the state of palmitoylation in the SH4 domain. J. Cell Sci. 122, 965-975), and attached to culture dishes during 2-3 d of culture in IMDM supplemented with 2.5% FBS and 2.5% horse serum.

Effects of DNA Compaction pH and PEI/DNA Ratios on Transfection Efficiency

HeLa cells were seeded into 35-mm culture dishes at $1\times10^5$ cells per dish and cultured for 1-2 days. The culture medium was replaced with fresh serum-containing medium before transfection. To form PEI/DNA polyplexes, 1 µg of pcDNA4-TO-EGFP was mixed with PEI in 100 µl of LBS or HBS at the PEI/DNA ratios described below, and the mixture was allowed to stand at room temperature for 20 minutes. In initial experiments 1 µg of pcDNA4-TO-EGFP and 5 µg of PEI were directly mixed in 100 µl of LBS, but in later experiments 1 µg of pcDNA4-TO-EGFP and 5 µg of PEI were separately diluted in 50 µl each of LBS and then mixed. The resulting PEI/DNA polyplexes were diluted with 500 µl of prewarmed serum-free IMDM, and added to each culture dish in a dropwise manner. At 24 hours post-transfection the cells were detached in phosphate-buffered saline (PBS) supplemented with 0.05% EDTA by gentle pipetting. After centrifugation, the cells were resuspended in PBS supplemented with 3% FBS and 1 µg/ml propidium iodide (PI), and EGFP fluorescence for protein expression and PI staining for dead cells were analyzed by flow cytometry using a MoFlo cell sorter (Beckman Coulter). Transfected cells grown in culture dishes were observed at 24 hours post-transfection under a Zeiss LSM 5 Pascal deconvolution microscope (Carl Zeiss).

Study for Transfection of a Cell Line Sensitive to PEI Cytotoxicity

HCT116 cells were sensitive to the toxicity of transfection reagents. To reduce toxicity of PEI and enhance the transfection efficiency, a sequential transfection method was developed. Specifically, the DNA/PEI polyplexes prepared with 7.5 µg of PEI and 6 µg of pCAG/TetR-IRES-CD25 were added to each 35-mm culture dish in a dropwise manner, and the culture medium was replaced with fresh serum-containing medium after 8 hours of incubation. For the subsequent transfection the DNA/PEI polyplexes prepared freshly were added to the cell culture, as described in the first transfection, and the medium was replaced again with fresh serum-containing medium after another 8 hours of incubation. Cells were further cultured for 16 hours and stained with anti-CD25 antibody, and the cell-surface expression of CD25 was analyzed by flow cytometry using a MoFlo cell sorter, as described previously (Nakayama, Y. et al., (2005) Multi-lobulation of the nucleus in prolonged S phase by nuclear expression of Chk tyrosine kinase. Exp. Cell Res. 304, 570-581).

Generation of Cell Clones that Stably Express EGFP

HeLa S3 cells were seeded in a 60-mm dish at $3\times10^4$ per dish and cultured for 1 day. To form PEI/DNA polyplexes, 97.5 µg of PEI and 15 µg of pcDNA4-TO-EGFP were separately diluted in 50 µl each of LBS (pH 3.5), and the dilutions were mixed and used for transfection, as described above. The cells grown in a culture dish for 24 hours after transfection were equally dispensed into four dishes, and stably transfected cells were selected in 250 µg/ml of Zeocin (Invitrogen) at 48 hours after transfection.

Example 1

Effects of acidic pH on stability of PEI during storage, formation of PEI/DNA polyplexes, and toxicity of PEI were studied.

Now, there are a large number of papers describing successful transfection with neutralized PEI solution. Actually in deed, an unpredictable decrease in the transfection activity of PEI is often observed when using PEI. Thus, the neutralized PEI solution is suspected to be unstable. Then, effect of acidic pH on stability of PEI during storage was studied.

When PEI was dissolved in HBS (pH 7.4), the transfection activity was severely decreased during one-month storage at 4° C. or –80° C. Specifically, taking the transfection activity immediately after preparation as 100%, the transfection activity was reduced to 0% after one-month storage, thus was completely lost. Moreover, dissolving PEI in ethanol drastically decreased its transfection activity within a couple of weeks during storage at 4° C. Specifically, taking the transfection activity at the time of preparation as 100%, the activity was reduced to 0% after a couple of weeks storage, thus was completely lost. Here, the transfection activity was evaluated after transfecting COS-1 cells with the vector containing EFGP gene as a ratio of the number of cells expressing EGFP gene to the number of all cells.

In sharp contrast, dissolving PEI in 0.2 N HCl that results in showing pH 1 preserved the full transfection activity for at least six months during storage at 4° C. or –80° C. Specifically, taking the transfection activity immediately after preparation as 100%, it was still 100% after six months storage.

Thus, it is likely that sufficient protonation of the amino groups of PEI in 0.2 N HCl may provide efficient protection against air oxidation. Meanwhile, the potential of PEI powder for transfection was lost to a great extent during storage at 4° C. or –80° C. once the bottle was opened. The air inside may start to oxidize PEI, giving rise to deterioration of the transfection activity.

Next, the effect of pH on polyplex formation was examined. In brief, polyplex formation was carried out using acidic and neutral compaction media followed by comparing the transfection efficiency. Specifically, PEI and pcDNA4-TO-EGFP were mixed in HBS (pH 7.4) or LBS (pH 3.5) so as to make the PEI/DNA ratio 5 (µg/µg), and the resulting PEI/DNA polyplex was transiently transfected into HeLa cells. At 24 hours post-transfection, EGFP expression was analyzed by flow cytometry. Transfection efficiencies were quantitated by counting the number of cells expressing EGFP at high levels and at low to high level As a result, the number of cells expressing EGFP upon use of LBS (pH 3.5) as compaction medium was much higher than that upon use of HBS (pH 7.4) (FIG. 1-A). Similar results were obtained from fluorescence microscopic observations (data not shown). It was reported that every sixth amino group is protonated at physiological pH where only a fraction of PEI is complexed with DNA, a half of amino groups are protonated at pH 5, and 80% of amino groups are protonated at pH 3 (Suh, J. et al., (1994) Ionization of poly(ethylenimine) and poly(allylamine) at various pH's. Bioorg. Chem. 22, 318-327; Clamme, J. P. et al., (2003) Monitoring of the formation and dissociation of polyethylenimine/DNA complexes by two photon fluorescence correlation spectroscopy. Biophys. J. 84, 1960-1968; Menzel, H. et al., (2003) Chemical properties of polyamines with relevance to the biomineralization of silica. Chem. Commun. 2003, 2994-2995). Accordingly, it is likely that the increased positive charge on PEI would promote the DNA/PEI polyplex formation.

In addition, the effect of acidic pH on toxicity of PEI was examined. HeLa cells transiently transfected with the polyplex formed in HBS (pH 7.4) or LBS (pH 3.5) were stained with PI and analyzed for PI-stained dead cells by flow cytometry.

As a result, LBS yielded a smaller number of dead cells stained with PI than HBS (FIG. 1-B), suggesting that use of LBS alleviates the toxicity of PEI. A significant part of toxicity results from free PEI molecules that do not form complexes with DNA (Godbey, W. T. et al., (2001) Poly(ethylenimine)-mediated gene delivery affects endothelial cell function and viability. Biomaterials 22, 471-480; Moghimi, S. M. et al., (2005) A two-stage poly(ethylenimine)-mediated cytotoxicity: Implications for gene transfer/therapy. Mol. Ther. 11, 990-995). Accordingly, enhancement of polyplex formation is likely to contribute to a decrease in the cytotoxicity.

The aforementioned results indicate that it is preferable to preserve PEI as an acidic PEI solution in order to maintain the stability during storage and thereby to obtain high transfection activity.

The aforementioned results also indicate that employing an acidic compaction medium but not a neutral compaction medium as a compaction medium for polyplex formation improves transfection efficiency and alleviates toxicity.

Example 2

Optimization of PEI/DNA ratios and compaction pH for polyplex formation were examined.

The transfection efficiency of PEI is dependent on a ratio of PEI to DNA (Non-Patent Document 2). Thus, PEI and DNA were mixed at various PEI/DNA ratios ranging from 1 to 10 in LBS (pH 3.5), and the resulting polyplex was used in comparison studies for transfection efficiency. Specifically, PEI and pcDNA4-TO-EGFP were mixed in LBS (pH 3.5) at various PEI/DNA ratios, and the resulting PEI/DNA polyplex was transiently transfected into HeLa cells. At 24 hours post-transfection, cells were stained with PI for detecting dead cells, and analyzed for EGFP expression and toxicity by flow cytometry.

The number of cells expressing EGFP was greatly increased at PEI/DNA ratios ranging from 5 to 8 (FIGS. 2-A and 2-B). The PEI/DNA ratio thus optimized corresponded to the ratio of nitrogen in PEI to phosphate in DNA (NP ratio) of 40 to 55 (FIG. 2-A), whereas linear low molecular weight PEI was used in neutral compaction medium at a preferred NP ratio of 6 (Non-Patent Documents 4 and 8; Ferrari, S. et al., (1997) ExGen 500 is an efficient vector for gene delivery to lung epithelial cells in vitro and in vivo. Gene Ther. 4, 1100-1106). The number of dead cells stained with PI was increased at a PEI/DNA ratio of 10 (FIG. 2-A). Excess free PEI molecules, which contribute to efficient transfection, inhibited the transfection efficiency through the high toxicity (FIG. 2-A; Clamme, J. P. et al., (2003) Monitoring of the formation and dissociation of polyethylenimine/DNA complexes by two photon fluorescence correlation spectroscopy. Biophys. J. 84, 1960-1968; Ira, M. Y. et al., (2003) DNA vector polyethyleneimine affects cell pH and membrane potential: A time-resolved fluorescence microscopy study. J. Fluoresc. 13, 339-347). Owing to excessive amounts of free PEI, large size vectors (>10 kbp) are preferable for efficient transfection at a low PEI/DNA ratio (~3) (data not shown).

Next, the effect of DNA compaction pH on transfection efficiency was examined. Specifically, PEI and pcDNA4-TO-EGFP were mixed at a ratio of 5 (μg/μg) in HBS (pH 7.4) or LBS (pH 3.5, 4.0, 4.5), and the resulting PEI/DNA polyplex was transiently transfected into HeLa cells.

As a result, the number of cells expressing EGFP was increased from two to six times when using LBS of pH3.5, pH4.0 and pH4.5 as compaction media compared to that when using HBS of pH7.4 (FIG. 2-C). In addition, it was found that LBS of pH 4.0 was the most efficient compaction medium (FIG. 2-C).

Therefore, it is recommended to use a compaction medium which pH is preferably from about pH 3.5 to about pH4.5, more preferably about pH 4.0, for example, LBS of such a pH level to achieve the highest level of PEI-mediated transfection efficiency.

Example 3

Transfection of various kinds of cells was examined by using PEI. As a result, HeLa, HeLa S3, A431, COS-1, MCF7, NIH3T3, HCT116 and HEK293 cells were successfully transfected with the PEI/DNA polyplexes formed in LBS (pH 4.0). The representative results are shown below.

COS-1 and HeLa S3 cells were transiently transfected with the polyplex formed by mixing 5 μg of pcDNA4-TO-EGFP with 25 μg of PEI (PEI/DNA ratio is 5) in LBS (pH 4.0), and after 12 hours of culture the medium was replaced with fresh serum-containing medium. Then, the EGFP expression was determined to evaluate transfection efficiency. As a result, transfection efficiencies in COS-1 and HeLa S3 cells were ~80% and ~60%, respectively (FIG. 3-A).

Next, the transfection efficiencies between PEI dissolved in LBS (pH 4.0) and TransIT-LT1, a commercial transfection reagent were compared. Specifically, cells were transiently transfected with the polyplex formed by mixing 1 μg of pcDNA4-TO-EGFP with 5 μg of PEI (PEI/DNA ratio is 5) in LBS (pH 4.0) or an optimal amount of TransIT-LT 1. Then, the EGFP expression was determined to evaluate transfection efficiency. As a result, it was found that the transfection efficiency using PEI transfection was comparable to that using TransIT-LT1 (FIG. 3-B).

Further, transfection of suspension cells with PEI was examined using human megakaryocytic Dami cells that are suspension culture cells. Since many suspension culture cells are poorly transfected using chemical transfection reagents, electroporation is usually performed with special equipment and a large number of cells in suspension, despite induction of massive cell death. Accordingly, transfection method using PEI/DNA polyplex formed by using acidified PEI under acidic conditions was studied for transfection of suspension cells. Since Dami cells were found to attach to culture dishes when they were grown in medium supplemented with FBS and horse serum (see materials and methods above), Dami cells in suspension culture were attached to culture dishes and transiently transfected with the polyplex formed by mixing 4 µg of pcDNA4-TO-EGFP with 26 µg of PEI (PEI/DNA ratio is 6) in LBS (pH 4.0). As a result, it was revealed that Dami cells were successfully transfected with the PEI/DNA polyplexes formed in LBS (pH 4.0) at a 3~5% transfection rate comparable to that by electroporation (FIG. 3C). The transfection method using PEI is useful for transfection of suspension cells in comparison to the transfection method using electroporation, since it does not require any special equipment and can be performed for a small number of cells.

Next, transfection of cells with PEI/DNA polyplex formed by using acidified PEI under acidic conditions was studied for cells highly sensitive to PEI exposure leading to cell aggregation and cell death. HCT116 cells were used as such a cell highly sensitive to PEI exposure. To reduce the toxicity of PEI, the PEI/DNA ratio was decreased to 1.25. Then, transfection procedure was carried out twice sequentially to increase transfection efficiency. Specifically, the cells were transiently transfected once or twice with the polyplex formed by mixing 6 µg of pCAG/TetR-IRES-CD25 with 7.5 µg of PEI in LBS (pH 4.0), and stained with anti-CD25 antibody followed by analyzing CD25 expression using a cell sorter. In brief, the DNA/PEI polyplexes prepared with 7.5 µg of PEI and 6 µg of pCAG/TetR-IRES-CD25 were added to each 35-mm culture dish in a dropwise manner, and the culture medium was replaced with fresh serum-containing medium after 8 hours of incubation. For the subsequent transfection the DNA/PEI polyplexes prepared freshly were added to the cell culture, as described in the first transfection, and the medium was replaced again with fresh serum-containing medium after another 8 hours of incubation. As a result, the sequential transfection procedure yielded a transfection efficiency of around 30%.

Since the high transfection efficiency and low cytotoxicity were attained by the transfection procedure using PEI/DNA polyplex formed by using acidified PEI under acidic conditions, it was examine whether stably transfected cell clones were easily generated. Specifically, stable transfection of HeLa S3 cells was carried out with the polyplex formed by mixing pcDNA4-TO-EGFP with PEI in LBS. Then, Zeocin-resistant colonies were cloned in 2 weeks. As a result, more than 200 single cell-derived colonies that stably expressed EGFP were obtained from $3 \times 10^4$ HeLa S3 cells (FIG. 3-E). Furthermore, stably transfected cell clones were successfully generated from PEI-sensitive HCT116 cells (data not shown).

In addition, the present transfection procedure using PEI was able to efficiently transfect various cell lines, including HeLa, COS-1 and Dami cells, with shRNA constructs for gene knockdown (data not shown).

INDUSTRIAL APPLICABILITY

The present invention can provide a method of introducing nucleic acids into cells which attains high transfection efficiency and minimum toxicity. Further, the method according to the present invention is cost-effective compared to the conventional method. In addition, the acidic PEI solution provided according to the present invention is stable and can preserve its transfection activity for a long time period, and therefore, can attain high transfection efficiency and minimum toxicity in introducing nucleic acids into cells.

The delivery of nucleic acids into cells is indispensable for basic research in molecular and cell biology as well as medical applications such as gene therapy. Thus, the present invention is useful and contributes to a wide range of fields from basic science to pharmaceutical research and development.

What is claimed is:

1. A reagent kit for introducing nucleic acids into cells, comprising a polyethyleneimine (PEI) solution consisting of PEI and 0.01 to 1N aqueous hydrochloric acid solution, wherein the PEI solution is of pH from 0.5 to 2.0.

2. The reagent kit for introducing nucleic acids into cells according to claim 1, wherein the aqueous hydrochloric acid solution is 0.2N aqueous hydrochloric acid solution.

3. The reagent kit for introducing nucleic acids into cells according to claim 1, wherein PEI being contained in the PEI solution is linear PEI.

4. The reagent kit for introducing nucleic acids into cells according to claim 1, wherein PEI being contained in the PEI solution is linear PEI with a molecular weight of 25,000.

5. The reagent kit for introducing nucleic acids into cells according to claim 1, wherein PEI being contained in the PEI solution is linear PEI with a molecular weight of from 10,000 to 50,000 and the aqueous hydrochloric acid solution is 0.2N aqueous hydrochloric acid solution.

6. A reagent kit for introducing nucleic acids into cells, comprising a polyethyleneimine (PEI) solution consisting of PEI and 0.01 to 1N aqueous hydrochloric acid solution, wherein the PEI solution is of pH from 0.5 to 2.0, and maintains efficiency in introducing nucleic acids into cells.

7. The reagent kit for introducing nucleic acids into cells according to claim 1, wherein PEI being contained in the PEI solution is linear PEI with a molecular weight of from 10,000 to 50,000.

8. The reagent kit for introducing nucleic acids into cells according to claim 1, wherein PEI being contained in the PEI solution is linear PEI with a molecular weight of from 10,000 to 25,000.

9. The reagent kit for introducing nucleic acids into cells according to claim 5, wherein the linear PEI has a molecular weight of from 10,000 to 25,000.

10. The reagent kit for introducing nucleic acids into cells according to claim 5, wherein the linear PEI has a molecular weight of 25,000.

11. A reagent kit for introducing nucleic acids into cells, comprising a polyethyleneimine (PEI) solution consisting of PEI and 0.01 to 1N hydrochloric acid, wherein the PEI solution is of pH from 0.5 to 2.0.

12. The reagent kit of claim 6, wherein aqueous hydrochloric acid solution is hydrochloric acid.

* * * * *

UNITED STATES PATENT AND TRADEMARK OFFICE
CERTIFICATE OF CORRECTION

| | | |
|---|---|---|
| PATENT NO. | : 9,249,417 B2 | Page 1 of 1 |
| APPLICATION NO. | : 13/936259 | |
| DATED | : February 2, 2016 | |
| INVENTOR(S) | : Naoto Yamaguchi and Yasunori Fukumoto | |

It is certified that error appears in the above-identified patent and that said Letters Patent is hereby corrected as shown below:

On the title page item (54) and in the specification, column 1, line 1,

"REAGENT KIT HAVING ACIDIFIED POLVETHVLENDIMINE FOR INTRODUCING NUCLEIC ACIDS INTO CELLS" should read -- REAGENT KIT HAVING ACIDIFIED POLYETHYLENEIMINE FOR INTRODUCING NUCLEIC ACIDS INTO CELLS --

Signed and Sealed this
Twelfth Day of April, 2016

Michelle K. Lee
*Director of the United States Patent and Trademark Office*